US006270746B1

(12) United States Patent
Katz

(10) Patent No.: US 6,270,746 B1
(45) Date of Patent: Aug. 7, 2001

(54) ASSAY FOR THE IDENTIFICATION OF IGE ANTIBODY SUPPRESSORS

(76) Inventor: David H. Katz, 1775 La Jolla Rancho Rd., La Jolla, CA (US) 92037-7848

( * ) Notice: Subject to any disclaimer, the term of this patent is extended or adjusted under 35 U.S.C. 154(b) by 0 days.

(21) Appl. No.: 09/251,175

(22) Filed: Feb. 17, 1999

(51) Int. Cl.[7] .......................... A61K 39/39; A61K 49/00; G01N 33/53; G01N 33/563

(52) U.S. Cl. .................. 424/9.2; 424/184.1; 435/7.1; 436/513

(58) Field of Search .................... 424/184.1, 9.2; 435/7.1; 436/513

(56) References Cited

PUBLICATIONS

Katz et al. Clinnical Allergy 9:609–624.*
Kerdine et al. Molecular Immunology 33(1):71–77.*
Bargate & Katz,"'Allergic Breakthrough'after antigen sensitization: height of IgE synthesis is temporally related to diurnal variation in endogenous steroid production," *J. Immunol.* 1980;125(5):2306–2310.
Bellanti, J.A., "Cytokines and allergic diseases: clinical aspects." *Allergy Asthma Proc* 1998;19(6):337–41.
Blaser, et al., "Investigation of a syngeneic murine model for the study of IgE antibody regulation with isologous antiidiotype antibodies," *Int Arch Allergy Appl Immunol*, 1981;64(1):42–50.
Chen, et al., "A Mouse Model of Mosquito Allergy for Study of Antigen–Specific IgE and IgG Subclass responses, Lymphocyte Proliferation, and IL–4 and IFN–γProduction," *Int. Arch. Allergy Immunol.* 1998;116:269–277.
Choi, et al. "Immunoglobulin E–dependent active fatal anaphylaxis in mast cell–deficient mice," *J Exp Med*, 1998;188(9):1587–92.
Chua, et al., "Epression of *Dermataphagoides pteronyssinus* Allergen, Der p II, in *Escherichia coli* and the Binding Studies with Human IgE," *Int. Arch. Allergy Appl. Immunol.* 1990;91:124–129.
Chua, et al., "Sequence Analysis of cDNA Coding for a Major House Dust Mite Allergen, Der p I Homology with Cysteine Proteases," J. Exp. Med 1988;167:175–182.
Claman, et al., "Immunoglobulin Dysregulation in Murine Graft–vs–Host Disease: A Hyper–IgE Syndrome." *Clin Immunol Immunopathol* 1990;56(1):46–53.
Cooper, D.A., "The immunological basis of immediate hypersensitivity," *Aust Fam Physician*, 1979;8(1):38–39, 41–43, 45–46.
Diaz–Sanchez, et al., "Ricin enhances IgE responses by inhibiting a subpopulation of early–activated IgE regulatory CD8+T cells," *Immunol*, 1993;78(2):226–36.
Dombrowicz, et al., "Anaphylasix Mediated Through a Humanized High Affinity IgE Receptor," *J. Immunol.* 1996;15:1645–1651.

Fung–Leung, et al., "Transgenic Mice Expressing the Human High–Affinity Immunoglobulin (Ig) E Receptor αChain Respond to Human IgE in Mast Cell Degranulation and in Allergic Reactions," *J Exp Med* 1996;183(1):49–56.
Katz, et al., "Regulation of IgE antibody production by serum molecules. V. Evidence that coincidental sensitization and imbalance in the normal damping mechanism results in 'allergic breakthrough,'" *J. Immunol.*, 1979;122(6)2191–2197.
Katz, et al., "The IgE antibody system: mature, peripheral B lymphocytes exert regulatory influences on the IgE systems of self–reconstituting, sublethally irradiated mice." *J Mol Cell Immunol*, 1984;1(2)83–9.
Katz, "IgE Antibody Responses in vitro: from Rodents to Man," *Prog. Allergy*1982;32:105–160.
Kawabata, et al., "Measurement of murine ovalbumin–specific IgE by a rat basophil leukemia cell serotonin release assay. Comparison to the rat passive cutaneous anaphylaxis assay." *j Immunol Methods*, 1993;162(1):9–15.
Marcelletti, et al., "IL–10 Stimulates Murine Antigen–Driven Antibody Responses *In Vitro* by Regulating Helper Cell Subset Participation." *Cell Immunol*, 1996;167(1):86–98.
Marcelletti, et al., "The Cellular Lesion Responsible for Exaggerated IgE Synthesis Accompanying Allergic Breakthrough." *Cell Immunol*, 1989;120(2):314–29.
Ohta, et al., "Human tonsillar IgE biosynthesis in vitro. I. Enhancement of IgE and IgG synthesis in the presence of pokeweed mitogen by T–cell irradiation," *J. Allergy Clin. Immunol.* 1983;7:212–223.

(List continued on next page.)

*Primary Examiner*—David Saunders
*Assistant Examiner*—Amy DeCloux
(74) *Attorney, Agent, or Firm*—Foley & Lardner; Stacy L. Taylor

(57) ABSTRACT

The invention provides an IgE and antigen-specific screening assay for use in identifying agents which suppress the IgE mediated immune response to antigen. The assay is performed in vivo in animals which hyper respond to antigen by producing exaggerated levels of IgE. The animals are sensitized to an antigen during a specific window of sensitivity which closes a day after the animal has been treated to produce the IgE hyper responsive phenotype. The screening assay is performed in the animals by treating them with a candidate IgE suppressor agent in conjunction with further immunization made after closure of the window of sensitivity defined by the invention. Positive results (indicating that the candidate agent has IgE suppressive activity) are obtained in the assay through measurement of a decline in antigen-specific IgE in the animal following its treatment with the candidate agent. The screening assay may also be utilized to measure other components of the immune response to antigen, including $IgG_1$ and $IgG_{2a}$ antibody production.

21 Claims, 1 Drawing Sheet

OTHER PUBLICATIONS

Peeters, et al., "Regulation of the IgE antibody response in Mice. II. Radioresistance of established IgE antibody production." *Immunol* 1981;43(1):25–32.

Rafnar, et al., "Cloning of *Amb a* I (Antigen E), the Major Allergen Family of Short Ragweed Pollen*" *J. Biol. Chem.* 1991;266:1229–1236.

Richards & Katz, "Analysis of the Promoter Elements Necessary for IL–4 and Anti–CD40 Antibody Induction of Murine FceRII (CD23)," *J.Immunol.* 1997;158:263–272.

Rizzo, et al., "Differential regulation of antigen presentation in high–and low–IgE responder mice," *Eur J Immunol*, 1991;21(7):1767–70.

Rogers, et al., "Recombinant Fel d I: Expression, Purification, IgE Binding and Reaction with Cat–Allergic Human T Cells," *Mol. Immunol.* 1993;30:559–568.

Santos–Argumendo, et al., "Antibodies to Murine CD40 Protect Normal and Malignant B Cells from Induced Growth Arrest," *Cell Immunol*, 1994;156(2):272–85.

Van Neerven, et al., "t Cell Epitopes of House Dust Mite Major allergen *Der p* II," *J. Immunol* 1993;151:2326–2335.

Vriesendorp, et al., "Immunoglobulin Levels in Dogs after Total–Body Irradiation and Bone Marrow Transplantation," *Transplantation* 1985;39:583–588.

Yang, et al., "CD8+T cells inhibit immunoglobulin E synthesis inlow responder SJL/J mice," *Immunol.*, 1998;93(2):230–237.

* cited by examiner

ASSAY FOR THE IDENTIFICATION OF IGE ANTIBODY SUPPRESSORS

STATEMENT REGARDING FEDERALLY FUNDED RESEARCH

The invention was made with support from the National Institutes of Health under NIH Grant No. AI-13874. The Government has certain rights in the invention.

FIELD OF THE INVENTION

The invention relates generally to the field of immunosuppressive drugs and screening assays for their identification. More specifically, the invention relates to a screening assay for use in identifying agents which suppress, selectively or non-selectively, the synthesis or activity of antibodies of the immunoglobulin E isotype (IgE).

HISTORY OF THE RELATED ART

IgE antibodies mediate aspects of the mammalian immune response to antigens which contribute toward the onset of an allergic attack. In susceptible individuals, IgE can induce a hypersensitive phenotype involving the excessive and rapid release of mediators such as histamine, slow-reacting substance of anaphylaxis and eosinophilic chemotactic factor leading, in the extreme, to potentially fatal conditions such as anaphylaxis.

Control of the IgE mediated immune response is therefore an important goal of allergy therapy, especially in immunotherapies directed to the induction of antigen tolerance through repeated antigen challenge of the host immune system. For the purposes of allergy therapy, the challenge is to suppress the host immune system in a manner which dampens the activity of IgE while retaining the protective and otherwise beneficial effects of all of the host other immune response to particular antigens. Thus, immunosuppressive agents which selectively target IgE mediated immune responses are potentially potent weapons in the arsenal against allergic disease.

SUMMARY OF THE INVENTION

The invention provides an screening assay for use in identifying agents which have potential for pharmaceutical use as suppressors of IgE mediated, antigen-specific immune responses to antigens. For use in the assay, an animal which hyper responds to antigen by producing exaggerated levels of IgE is prepared or otherwise obtained. Initial sensitization of the animal to antigen is made within a specific, time-limited window of sensitivity defined by the invention. The animal thereafter maintains exaggerated IgE responsiveness to the sensitizing antigen, despite its return to an otherwise normal IgE phenotype.

Identification of potential IgE suppressors is performed in the animal by treating it with the candidate suppressor with or following primary immunization. A decline in antigen-specific IgE levels following treatment indicates that the candidate possesses suppressive activity. The scope of useful information provided by the assay can be expanded through measurement and comparison of other indicia of IgE immune responsiveness in the animal, such as levels of markers of the Th2 immunophenotype in which IgE production is normally induced.

To these ends, in one aspect of the invention, the animal platform for the screening assay is a non-human mammal whose IgE-mediated allergic system correlates with the IgE-mediated allergic systems of humans.

In another aspect of the invention, the non-human mammal is a rodent.

In another aspect of the invention, the rodent is a mouse.

In another aspect of the invention, the animal platform is rendered hyper responsive to antigen through low dose irradiation.

In another aspect of the invention, successful induction of an IgE hyperresponsive phenotype in the animal platform for the screening assay is confirmed through ablation of such responsiveness with $CD23^+$ B cells delivered to the animal during the window of sensitivity defined by the invention.

DETAILED DESCRIPTION OF THE INVENTION

I. Advantages Offered by the Invention

Figure 1:
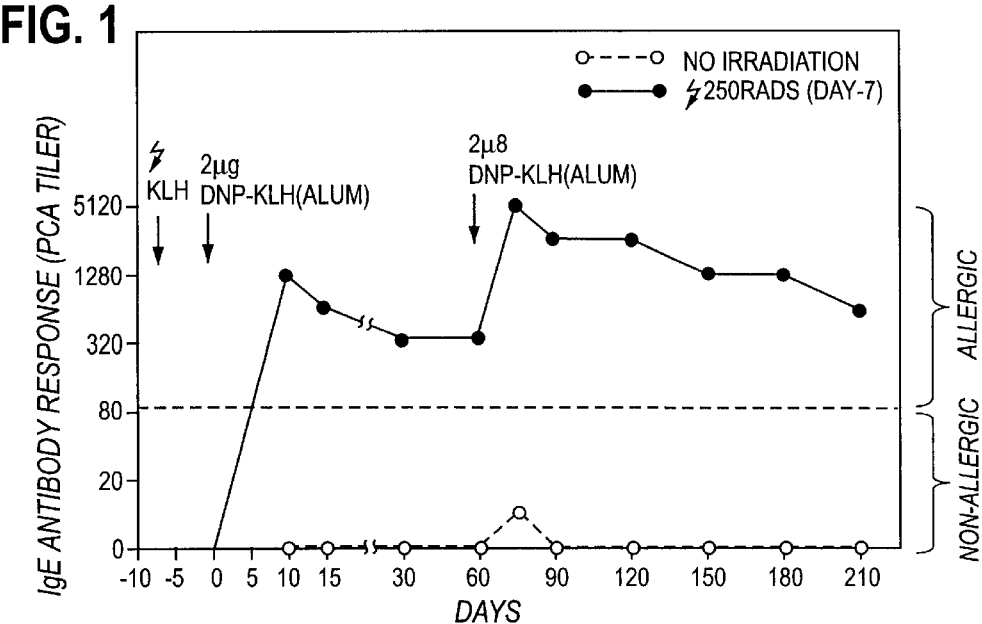
FIG. 1 shows data demonstrating allergic breakthrough in the context of the IgE-mediated immune response of SJL/J ($H-2^s$) mice irradiated and immunized as described herein.

The invention consists of a practical application of the "allergic breakthrough" hypothesis for acquisition of IgE mediated allergy in mammals. According to the allergic breakthrough hypothesis, animals who have not previously exhibited an IgE-mediated allergic phenotype will do so on contact with antigen if the native dampening mechanism which controls their IgE antibody production is overcome under circumstances favoring acquisition of allergy.

With respect to such circumstances, a remarkable and surprising discovery leading to the invention was the realization that the allergic breakthrough phenomenon is dependent upon the timing of initial sensitization of an animal to an antigen in relation to the loss of regulatory control over IgE production in the animal. In particular, for allergic breakthrough to occur, such initial sensitization must take place within a day of the loss of regulatory control—a short and fairly rigid window of sensitivity whose existence could not have been predicted from simple observation of IgE responses to antigen.

More specifically, if the animal's sensitization to antigen takes place beyond the window of sensitivity defined by the invention, the animal will not acquire the exaggerated IgE responsiveness which characterizes allergic breakthrough. However, if sensitization occurs before closure of the window of sensitivity, not only will enhancement of the IgE response to the antigen occur, but it will be retained even after the animal returns to an otherwise normal level of IgE responsiveness to other antigens. Thus, the invention provides the parameters by which allergic breakthrough can be induced and exploited as a tool for identification of antigen-specific IgE suppressors.

For use in evaluating IgE selective suppressors, the invention further provides means of inducing exaggerated IgE responsiveness in an animal while the animal's other immune functions remain relatively unaffected. In this respect, the invention provides an in vivo environment in which the immune response can be induced, measured and targeted for IgE and antigen selective suppression.

II. Methods for Performance of Screening Assay

A. Animal Platforms

The animal utilized as a platform for the screening assay can be any animal whose IgE mediated immune system is susceptible to disruption by environmental influences such as sublethal radiation and certain toxins. Among such animals, those whose IgE mediated allergic systems correlate well with the human system are the better choices for use in the screening assay of the invention. The animal chosen may, but need not, be immunologically naive with respect to the immunizing antigen selected for study.

Mice offer a cost-effective, easily obtained model which correlates well with the human IgE mediated immune response at the physiological and molecular levels (see, c.g., Katz, *Prog.Allergy*, 32:105–160, 1982; and, Richards and Katz, *J.Immunol.*, 158:263–272, 1997). Any species of mouse can be utilized effectively in the screening assay, but those which are known to be low IgE responders are especially useful in that measurement of increases and declines of IgE levels is simplified by the low background levels of IgE usually produced in the animals. Mice of the SJL/J, C57BL/6(H-$2^b$) and DBA/2 strains (with an IgE responsiveness at or below 80 PCA titer of 80) are examples of low IgE responder animals, and can be purchased commercially through sources such as Jackson Labs (based in Maine) and Charles River Labs (based in Massachusetts).

Those of ordinary skill in the art will be familiar with, or can readily ascertain, the identity of additional suitable animal models of human IgE-mediated allergy, including low IgE responder animals. The susceptibility of such animals to IgE immune modulation, if not known, can be determined through treatment of the animal with an IgE immune enhancer and measurement of the effect of the enhancer on the animal through conventional assay measurements of its IgE immune response (see, e.g., with respect to specific animals, Katz, *Prog.Allergy*, 32:105–160, 1982 [rodents]; Chen, et al., *Int.Arch.Allergy Immunol.*, 116:269–277, 1998 [murine model of anaphylaxis]; Ohta, et al., *J.Allergy Clin.Immunol.*, 7:212–223, 1983 [antigen-stimulated human B cells]; Vriesendorp, et al., *Transplantation*, 39:583–588, 1985 [susceptibility of dogs to IgE immune response modulation by sublethal irradiation]; Dombrowicz, et al.,*J.Immunol.*, 15:1645–1651, 1996 [transgenic animal models of the human IgE immune system]).

B. Preparation of Animal Platform for Screening Assay

Certain environmental influences ("IgE enhancers"), such as sublethal irradiation and toxins such as ricin (castor bean lectin), have significant stimulatory effects on IgE responses to antigen. For use in developing exaggerated IgE responsiveness in the animal platform of the invention, sublethal irradiation is a convenient choice whose physiological effect is well-characterized (for example, low-dose irradiation has been used therapeutically in humans and experimentally in lower animals).

While exposure to high levels of radiation tends to have an overall immunosuppressive effect on mammals, the invention provides the discovery that exposure to discrete and relatively low doses of radiation coupled with antigen immunization will greatly enhance IgE responsiveness to antigen if irradiation and immunization occur within the correct temporal relationship; i.e., immunization should follow within about 24 hours of irradiation. The same temporal limitation applies to other IgE enhancers as well, indicating that the optimal sensitivity of activated IgE producing B cells to antigen sensitization lies within a 24 hour window which opens upon disruption of the animal's IgE dampening mechanisms.

Diurnal variations also play a role in optimization of IgE producer cell sensitivity to nonantigen stimulation. The sensitivity of IgE producer B cells to IgE enhancers such as irradiation is greatest in mice when accompanied by low levels of endogenous corticosteroids occurring at particular times of the day. For example, in SJL/J mice, IgE enhancement through whole-body irradiation is greater during the early afternoon (12:00 p.m. to 4:00 p.m.), when circulating levels of corticosteroids are at a natural low, than at other times of the day (for more details in regard to diurnal variations in mice and the effect on IgE responsiveness, see, e.g., Bargatze and Katz, *J. Immunol.*, 125:2306–2310, 1980). Thus, the time of day that the IgE enhancer is administered to an animal can effect the magnitude of the enhancement in IgE levels obtained, while the temporal relationship between the administration of the enhancer and antigen determines whether enhanced IgE levels are obtained at all.

To these ends, the animal to be utilized in the screening assay of the invention is treated with an IgE enhancer, then immunized within a day. Where the IgE enhancer is whole-body irradiation, the dose administered will necessarily be sublethal and should also be sub therapeutic. The optimal level may vary from species to species, but will generally fall below 700 rads, and desirably will fall within the range of 150–400 rads. Those of ordinary skill in the art will be familiar with, or can readily ascertain, suitable protocols for administration of sublethal, whole-body irradiation or other IgE enhancers, an example of which is provided elsewhere below.

C. Immunization of Animals

The immunogen chosen will vary with the clinical interests and goals of the practitioner, and may be comprised of an allergen, Th2 stimulatory infectious agent, immunogenic epitope, allergen extract or polynucleotide encoding an immunogenic (for convenience, the population of immunogenic substances which may be utilized in the invention will be referred to herein as "antigens", unless context otherwise requires, but it will be understood that the immunization steps of the invention are not limited to delivery of antigens per se). Common allergens responsible for a relatively high incidence of IgE-related allergic events in humans include the IgE reactive major dust mite allergens Der pI and Der pII (Chua, et al., *J.Exp.Med.*, 167:175–182, 1988; and, Chua, et al., *Int.Arch.Allergy Appl. Immunol.*, 91:124–129, 1990); T cell epitope peptides of the Der pII allergen (Joost van Neerven, et al., *J.Immunol.*, 151:2326–2335, 1993); the highly abundant Antigen E (Amb aI) ragweed pollen allergen (Rafnar, et al., *J.Biol.Chem.*, 266:1229–1236, 1991); phospholipase $A_2$ (bee venom) allergen; the Fel dI major domestic cat allergen (Rogers, et al., *Mol.Immunol.*, 30:559–568, 1993); and, food allergens, notably the peanut and tree nut allergens. Model antigens accepted in the art as such, including ovalbumin (OVA), keyhole limpet hemocyanin (KLH) and conjugates thereof (e.g., with 2-dinitrophenyl [2-DNP]), are also well suited for use in invention.

Those of ordinary skill in the art will be entirely familiar with acceptable means of immunizing animals including, without limitation, means for immunization by intravascular, subcutaneous, intramuscular, intraperitoneal, nasal, topical and opthalmic routes of administration. Extensive protocols for immunizing animals for use in the invention are therefore not provided here.

Briefly, the antigen may be delivered in carrier (e.g., sterile saline), with or without an adjuvant, such as alum. The animal is sensitized to the antigen within a day, and desirably within 6–10 hours, of treatment of the animal with an IgE enhancer. Primary immunization with an immunologically related antigen (described further below) is made at a point in time after treatment of the animal with the IgE enhancer; conveniently, primary immunization will occur at about a week post-sensitization. Primary immunization may be followed by further immunizations with the same or immunologically related antigens to permit evaluation of the effect of the candidate IgE suppressor on the animal's response to subsequent antigen challenge.

It will be appreciated that the initial sensitizing antigen must share immunological activity with the antigen utilized in subsequent immunizations to permit evaluation of the animal's response of immunization and treatment following sensitization. In particular, to permit processing of antigen in later immunizations in a manner equivalent to processing of the antigen on initial sensitization, the antigens utilized in each immunizing step should share at least immunogenic epitopes (e.g., sensitization can be with whole antigen, followed by an immunogenic extract or fragment of the same, or vice-versa, so long as immunogenicity of the immunogens delivered in each step is comparable). Such antigens are those referred to herein as being "immunologically related".

Where immune responses to more than one antigen are to be evaluated in the screening assay, the second antigen may be delivered in the initial sensitization step and on primary immunization, or only during the latter step, but if not delivered during the sensitization step, must be conjugated to the sensitizing antigen or otherwise delivered in a manner which permits both antigens to be processed by the animal's immune cells in similar fashion. An example of this approach is described in Example I below, where sensitization of an animal to KLH is followed by primary immunization with a KLH-DNP (2-dinitrophenyl) conjugate.

In the example provided, the KLH molecule in the conjugate delivered in the primary immunization step is "immunologically related" to the sensitizing KLH antigen. Because the DNP molecule is conjugated to the KLH molecule, it will be processed by the animal in a manner similar to the processing of the KLH molecule even though DNP is antigenically different from KLH. Thus, although the animal was not sensitized to DNP during the window of sensitivity, it will be "seen" by the animal's cells as immunologically related to KLH as both molecules are processed together as a consequence of their delivery as a conjugate—a single immunogenic moiety. As such, in this example, the exaggerated IgE response achieved in the primary immunization step will be specific to both KLH and DNP. However, if DNP is delivered independently of KLH in the primary immunization step, it will not be seen by the animal as immunologically related to the KLH sensitizing antigen, and the exaggerated IgE response will be directed only to KLH. In this manner, multiple antigens may be delivered to the animal, and evaluated accordingly, in the primary immunization step of the inventive screening assay.

Those of skill in the art will be familiar with, or can readily ascertain, methods for delivery of multiple immunogens to an animal as a single immunogenic moiety (e.g., by conjugation or co-delivery in a liposome), or can obtain suitable compositions for use in this regard from commercial sources.

D. Performance of the Screening Assay of the Invention

Following initial sensitization to antigen of an animal prepared for use in the screening assay as described above, the primed animal is treated (more than 24 hours after its exposure to an IgE enhancer) with a candidate IgE suppressor or, for use as a control, with vehicle. Primary immunization with the sensitizing antigen is desirably made with, but may be made at a time before, delivery of the candidate IgE suppressor.

At set time points before and after primary immunization (as well as before treatment with the IgE enhancer, if possible), an immune sample is taken from the animal and analyzed for antigen-specific and total levels of IgE. Depending on the antigen and its route of administration to the animal, the immune sample may consist of fluids such as serum, bronchoalevolar lavage and mucosal swabs. IgE levels are determined by conventional assays, many of which are commercially available in the art and will be familiar to those of ordinary skill in the art. An example of such an assay is provided in the Examples elsewhere below.

Other aspects of the IgE mediated immune response may also be examined in the assay. In this respect, those of ordinary skill in the art will understand that IgE antibodies are principally produced in the context of a "Th2 phenotype"; i.e., an immune phenotype associated with the extracellular exposure of a host to antigen and characterized by the activation of class 2 helper T lymphocytes. Th2 responses include the allergy-associated IgE antibody class; soluble protein antigens tend to stimulate relatively strong Th2 responses. In contrast, Th1 responses are induced by antigen binding to macrophages and dendritic cells.

IgG, antibodies are serological markers for a Th2 type immune response, whereas $IgG_{2a}$ antibodies are indicative of a Th1 type immune response. The Th2 immune phenotype is further characterized by the release of certain cytokines; e.g., IL-4, while the Th1 immune phenotype tends to be accompanied by the release of cytokines such as IL-12 and/or an increase in IFN ($\alpha$, $\beta$ or $\gamma$) levels). Because the helper T lymphocyte system negatively reciprocates between the Th2 and Th1 classes of Th cells, a rise in levels of Th1 cytokines (e.g., IL-12 and IFN $\alpha$, $\beta$ or $\gamma$) and/or of $IgG_{2a}$ antibodies correlates to suppression of the Th2 phenotype and, consequently, of a decline in the animal's ability to mount an IgE-mediated immune response.

Thus, the screening assay of the invention may also be applied to obtaining, circumstantial evidence of IgE suppression by a candidate compound gleaned from determining the class of helper T lymphocyte-mediated immune phenotype present before and after primary immunization and treatment with the candidate IgE suppressor. In particular, declines in Th2 cytokine and $IgG_1$ antibody levels and increases in Th1 cytokine and $IgG_{2a}$ antibody levels are indicia of probable Th2 phenotype induction/IgE suppression; the reverse profiles are indicative of Th2 phenotype induction/IgE stimulation.

Comparative measurements of antibody isotypes other than IgE (pre- and post-primary immunization), as well as other antigen-sensitive immune components (cytokines, effectors, eosinophil infiltrate levels and the like) will provide information as to the relative sensitivity of the candidate IgE suppressor; i.e., as to whether it affects only IgE production/activity or whether other aspects of the immune system are also affected (desirably or not). In the murine animal platform of the invention utilizing low IgE responder animals, however, the assay can be expected to have a high degree of specificity for the IgE immune system; e.g., effects on total IgG responses can be expected to be meager.

All of these immune components can be detected and measured by conventional assays, many of which are commercially available to the art and will be familiar to those of ordinary skill in the art. Example of such assays are provided in the Examples elsewhere below and include an ELISA for the $IgG_1$ and $IgG_{2a}$ isotypes using subclass-specific antibodies; an ELISA for antigen-specific and total IgE (Coligan, "Current Protocols In Immunology", Unit 7.12.4, Vol. 1, Wiley & Sons, 1994); a sensitive (0.4 ng of IgE/ml) solid phase radioimmunoassay (RAST) modification of the IgE ELISA (substituting purified polyclonal goat antibodies specific for mouse $\epsilon$ chains for antibodies specific for human Fab); and, an anti-CD3 antibody (Pharmingen, La Jolla, Calif.) based splenocyte assay in which supernatants are assayed for cytokine levels (e.g., IL-4, IL-10 and IL-12) levels using a commercial kit, and interferon (e.g., INF$\gamma$) levels are assayed with an anti-INF$\gamma$ murine antibody assay (see, e.g., Coligan, "Current Protocols in Immunology", Unit 6.9.5., Vol. 1, Wiley & Sons, 1994).

Those of ordinary skill in the art will also recognize that an abbreviated protocol for the screening assay of the invention can be devised to test the activity of IgE enhancers. In particular, with measurement of IgE levels following treatment of an animal with a putative IgE enhancer and its priming with antigen, the failure of an animal which should develop an IgE hyperresponsive phenotype to do so is evidence that the putative IgE enhancer does not possess that activity, at least in the animal utilized in the assay.

Although not limited by any theory as to how IgE enhancement occurs in the animals utilized by the screening assay to evaluate IgE suppression, it appears that IgE enhancers such as low dose irradiation temporarily limit IgE binding by $CD23^+$ (F$\epsilon$cRII) B cells. Binding of IgE by B cells through the CD23 receptor regulates their differentiation and controls the onset of the IgE-mediated allergic phenotype. Thus, disruption of IgE binding by $CD23^+$ B cells allows IgE-mediated responses to antigen to proceed unabated by $CD23^+$ B cell regulation.

This probable explanation for the biological effect of IgE enhancers on host B cells suggests that the screening assay of the invention will be of particular use in evaluating agents which overcome the radiation-mediated perturbation of IgE binding by $CD23^+$ B cells (such as ex vivo preparations of such cells). In addition, transplanted $CD23^+$ B cells, or any other agent known to have IgE suppressive activity (e.g., isolated or synthetic $CD23^+$ peptides including the IgE binding domain, or anti-IgE antibodies) can be used to verify the viability of the animal platform in that such cells can ablate IgE production and activity if administered during the window of sensitivity.

Examples illustrating the practice of the invention are set forth below. The examples are not intended to, and do not, limit the scope of the invention, which is defined by the appended claims.

EXAMPLE I

IRRADIATION-ENHANCED In Vivo IgE ANTIBODY RESPONSES

As proof of the principle that exaggerated IgE levels can be produced in an antigen-specific and time-specific manner, two groups of low IgE responder SJL/J (2-H$^s$) mice were prepared as follows: Group I was irradiated at 250 rads shortly before priming immunization with 2 $\mu$g of KLH in alum hydrogen peroxide (Pierce Chemical; a Th2 stimulatory adjuvant). The second group received the priming dose of KLH in alum, but was not irradiated. Seven days later (day 0), each group received 2 $\mu$g of DNP-KLH conjugate in alum and antigen-specific IgE levels were measured by ELISA in serum samples drawn from each mouse. Secondary antigen challenge was made on day 60 using the same antigen and dose given for primary immunization on day 0. Antigen-specific IgE were again measured at days 7, 14, 21, 60, 75, 120, 150 and 210.

Results are shown in FIG. 1, where IgE levels are represented as PCA titers. Anti-antigen IgE responses induced in the irradiated animals through irradiation-concomitant priming followed by primary immunization a week later were more than 1000 times the magnitude of IgE levels produced in the non-irradiated animals, and nearly 5000 times the magnitude following secondary immunization, indicating that the antigen-specific IgE responsiveness in the irradiated animals was not only induced, but maintained at allergic levels over time and on subsequent antigen challenge.

To determine the antigen-specificity of the exaggerated IgE response of the irradiated animals, two additional groups of animals were prepared and immunized as described above through day 0, except that irradiation was applied to the treatment group at 350 rads. On day 18, one group of the irradiated and untreated mice were secondarily immunized with the primary immunogen (2 $\mu$g DNP-KLH in alum), while a second group of irradiated and untreated mice received a different antigen—10 $\mu$g of OVA in alum. IgE responses to the DNP-KLH antigen were determined prior to and after primary immunization as well as at secondary immunization; anti-OVA IgE were also measured on days 28 and 35.

Figure 2:
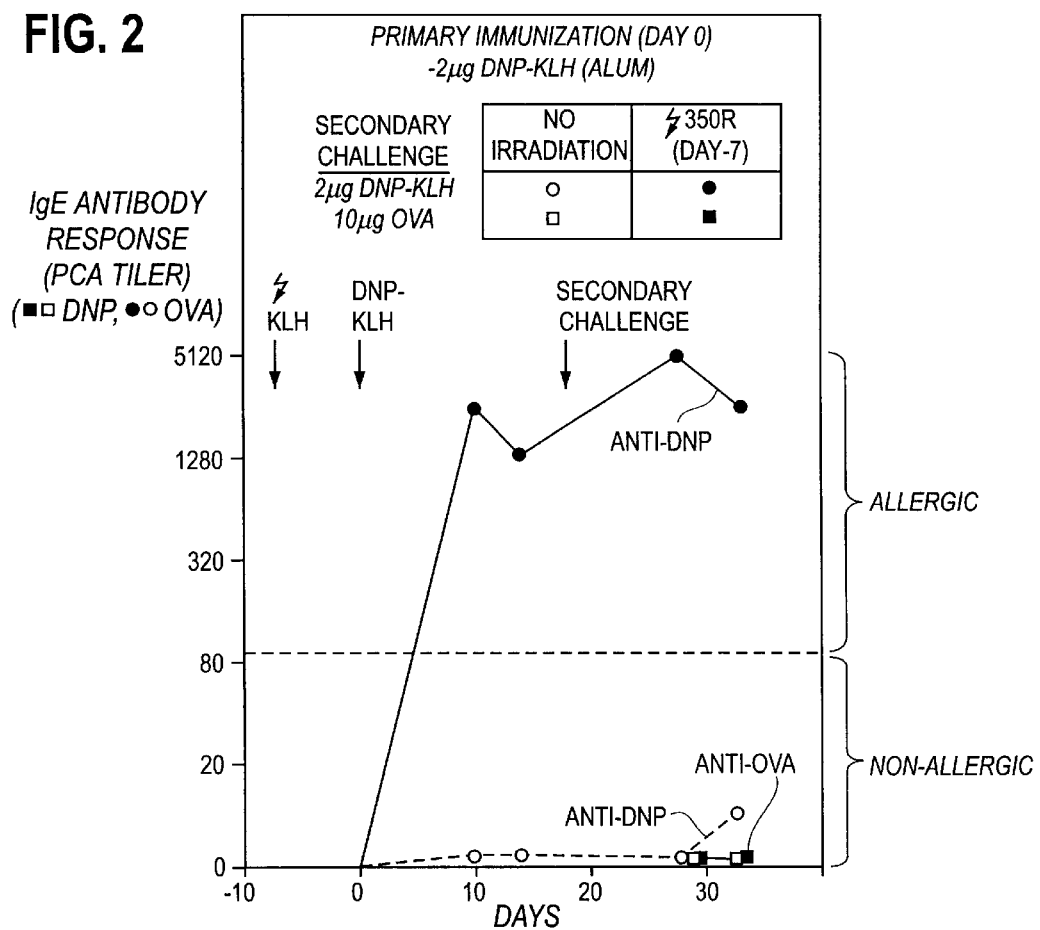
FIG. 2 shows data demonstrating the exclusion of antigens other than the primary immunogen from the exaggerated IgE responses of the mice described in FIG. 1.

Results are shown in FIG. 2, where IgE levels are represented as PCA titers. Significantly, there was no detectable difference in the anti-OVA IgE produced in the irradiated and untreated mouse sets, even though there were dramatic differences in the anti-DNP IgE produced in irradiated versus untreated mouse groups (comparable to the responses shown in FIG. 1). Thus, the exaggerated antigen responsiveness in the IgE compartment of the irradiated mice was not retained with respect to antigens other than the primary immunogen following priming and allergic breakthrough.

With application of an active IgE suppressor at or near primary immunization, antigen-specific IgE can be expected to fall toward normal levels in the animal. For example, in low IgE responder mice, complete ablation of the exaggerated IgE response by an IgE suppressor would return the antigen-specific IgE levels to a magnitude comparable to that achieved in unirradiated mice and irradiated mice immunized outside of the window of sensitivity (data not shown).

The invention having been fully described, modifications and extensions of it may become apparent to those of ordinary skill in the art. All such modifications and extensions are intended to fall within the scope of the claimed invention.

The invention claimed is:

1. A screening method for identifying agents having IgE suppressor activity, the method comprising:
    (a) determining the IgE responsiveness to antigen of an animal before and after administration to the animal of a candidate IgE suppressor, wherein the animal has been treated with an IgE enhancer prior to performance of the screening method, the steps for determining such IgE responsiveness comprising:
        (i) sensitizing the animal to a sensitizing antigen within a day of treatment of the animal with the IgE enhancer;
        (ii) delivering a primary immunization dose of an antigen to the animal, wherein the antigen is immunologically related to the sensitizing antigen;
        (iii) measuring levels of IgE in the animal;
        (iv) delivering the candidate IgE suppressor to the animal; and,
        (v) measuring levels of IgE in the animal; then, (b) comparing the measurements obtained in step (a)(iii) with the measurements obtained in step (a)(v), wherein a decline in any of the measured values so compared indicates that the candidate IgE suppressor suppresses the production and/or activity of IgE in the animal.

2. The method according to claim 1 wherein the IgE enhancer is sublethal, whole-body irradiation.

3. The method according to claim 2 wherein the irradiation is performed at a level between 150 and 400 rads.

4. The method according to claim 1 wherein the animal in which IgE responsiveness is determined is a rodent.

5. The method according to claim 4 wherein the rodent is a mouse of the low IgE responder phenotype.

6. The method according to claim 1 wherein the animal in which IgE responsiveness is determined is one whose IgE mediated immune system correlates to the human IgE mediated immune system to an extent sufficient that the performance of a candidate IgE suppressor in the animal can be reasonably predicted to behave similarly in humans.

7. The method according to claim 1 wherein step (a)(ii) is performed within 7 days of the performance of step (a)(i).

8. The method according to claim 7 wherein step (a)(v) is performed within 14 days of the performance of step (a)(ii).

9. The method according to claim 1 wherein steps (a)(iii) and (a)(iv) are performed on the same day as step (a)(ii).

10. The method according to claim 1 further comprising the steps (a)(iii)', (a)(v)' and (b)' wherein the levels of at least one marker for the Th2 immunophenotype are also measured in steps (a)(iii)' and (a)(v)' and then compared in step (b)'.

11. The method according to claim 1 further comprising the steps (a)(iii)', (a)(v)' and (b)' wherein the levels of at least one marker for the Th1 immunophenotype are also measured in steps (a)(iii)' and (a)(v)' and then compared in step (b)'.

12. The method according to claim 1 further comprising the steps (a)(iii)', (a)(v)' and (b)' wherein the levels of at least one of the $IgG_1$ and $IgG_{2a}$ subclasses are also measured in steps (a)(iii)' and (a)(v)' then compared in step (b)'.

13. The method according to claim 1 wherein the animal has been treated with an IgE enhancer during the time of day in which the animal is known or determined to have lower levels of endogenously produced corticosteroids than at other times of the day.

14. The method according to claim 1 wherein the sensitization of step (a)(i) is performed within 6 to 10 hours of treatment of the animal with the IgE enhancer.

15. The method according to claim 2 further comprising the step (a)(i)', wherein the effect of the irradiation on the IgE responsiveness of the animal is confirmed by: (1) measuring levels of IgE in the animal after delivery of the primary immunization dose of antigen; (2) treating the animal with an IgE suppressor after delivery of the primary immunization dose of antigen to the animal but before the expiration of the 24 hour period following irradiation, wherein further the ablation of any IgE measured in the animal during step (a)(i)'(1) confirms that the desired effect of the irradiation on the animal's IgE responsiveness has occurred.

16. The method according to claim 15 wherein the IgE suppressor is a CD23+ cell.

17. The method according to claim 15 wherein the IgE suppressor is an anti-IgE antibody.

18. The method according to claim 15 wherein the IgE suppressor is a CD23+ peptide containing an IgE binding domain.

19. The method according to claim 1 wherein the levels of IgE measured in steps (iii) and (v) are of total IgE.

20. The method according to claim 1 wherein the levels of IgE measured in steps (iii) and (v) are of antigen-specific IgE.

21. The method according to claim 1 wherein the levels of IgE measured in steps (iii) and (v) are of total IgE and of antigen-specific IgE.

* * * * *